United States Patent [19]

Avrameas et al.

[11] 4,241,176

[45] Dec. 23, 1980

[54] MAGNETIC GEL SUITABLE TO IMMUNOENZYMATIC DETERMINATIONS

[75] Inventors: Stratis Avrameas, La Celle Saint Cloud; Jean-Luc Guesdon, Paris, both of France

[73] Assignee: Etablissement declare d'Utilite Publique diti Institut Pasteur, Paris, France

[21] Appl. No.: 928,944

[22] Filed: Jul. 28, 1978

Related U.S. Application Data

[63] Continuation of Ser. No. 746,553, Dec. 1, 1976, abandoned.

[30] Foreign Application Priority Data

Dec. 2, 1975 [FR] France .............................. 75 368891

[51] Int. Cl.$^3$ ........................ C12Q 1/66; C07G 7/00
[52] U.S. Cl. ................................ 435/7; 260/112 R; 435/176; 435/181
[58] Field of Search ................ 23/230 B; 195/99, 127, 195/103.5 A; 424/2, 12; 435/7, 174, 176, 178, 181; 260/112 R

[56] References Cited

U.S. PATENT DOCUMENTS

| | | | |
|---|---|---|---|
| 3,788,950 | 1/1974 | Hicks et al. | 435/181 |
| 3,843,450 | 10/1974 | Saxholm | 195/103.5 A X |
| 3,966,897 | 6/1976 | Renn et al. | 424/12 X |
| 3,970,518 | 7/1976 | Giaever | 424/12 X |
| 3,979,184 | 9/1976 | Giaever | 424/12 X |
| 4,048,018 | 9/1977 | Coughlin et al. | 435/176 |
| 4,070,246 | 1/1978 | Kennedy et al. | 435/181 |
| 4,108,972 | 8/1978 | Dreyer | 424/8 |

FOREIGN PATENT DOCUMENTS 1403359 8/1975 United Kingdom .

OTHER PUBLICATIONS

Chaplin et al., "Magnetic, Immobilized Derivatives of Enzymes," *Chem. Abstracts*, vol. 85, (1976), p. 203, Abs. No. 188415w.

Heden et al., "The Potential of Magnetic Separation of Biologically Active Proteins", *Biotechmol. & Bioeng. Symp.* No. 3, (1972), pp. 173-174.

Mosbach et al., *Methods in Enzymology*, vol. 44, Academic Press, New York, pp. 324-326.

Dunnill et al., "Purification of Enzymes Using Magnetic Bio-Affinity Materials", *Biotech & Bioeng.*, vol. 16, (1974), pp. 987-990.

Guesdon, et al., "Magnetically Responsive Polyacrylamide Agnrose Beads for the Preparation of Immunoabsorbents", *J. Immuno., Meth.*, vol. 21, (1978), pp. 59-63.

Guesdon, et al., "Dosages Immuno.-Enzymatiques des Ig E", *Annales Medicales de Nancy*, pp. 33-38.

Guesdon, et al., "Magnetic Enzyme Immunonssay for Measuring Human Ig E.", *J. Allergy Chin. Immunol.*, vol. G1, No. 1, (1978), pp. 23-27.

*Primary Examiner*—Thomas G. Wiseman
*Attorney, Agent, or Firm*—Sprung, Felfe, Horn, Lynch & Kramer

[57] ABSTRACT

The invention relates to a magnetic gel which is useful for immunoezymatic determinations.

Said gel consisting, for example, of polyacrylamideagarose and magnetic particles, coupled with an antibody, can be used for rapid determinations of the antigens contained in a biological liquid, the presence of magnetic particles permitting rapid separation of the gel from the reaction medium by means of a magnetic field and considerably shortening the time required for determinations.

5 Claims, 1 Drawing Figure

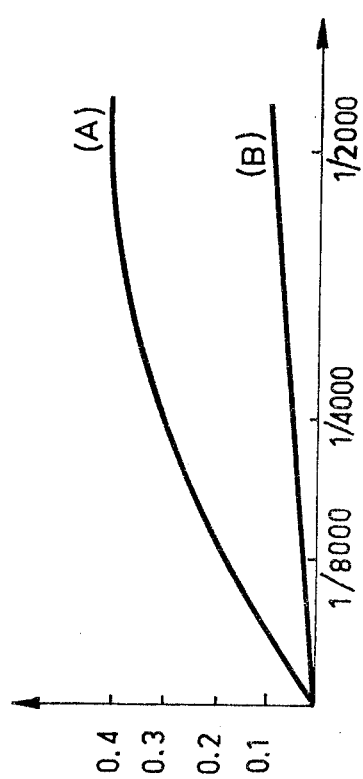

MAGNETIC GEL SUITABLE TO IMMUNOENZYMATIC DETERMINATIONS

This is a continuation of application Ser. No. 746,553, filed Dec. 1, 1976, now abandoned.

The present invention relates to the field of the determination of the amounts of proteins, for example antigens and antibodies, which are present in certain biological media. The object of the invention is more particularly a magnetic gel comprising acrylamide, agarose or acrylamide-agarose, a process for obtaining same and its use in immunoenzymatic quantity determinations; the magnetic gel according to the invention makes it possible to effect rapid immunoenzymatic determinations.

The detection of antibodies and antigens by means of enzymes is a known process (see Bull. Soc. Chim. Biol. 1968, 50, no. 5–6). Processes have also already been described for revealing and determining a component of a reaction between a specific binding protein and the corresponding bindable substance by labelling the latter by means of an enzyme; according to such processes determination of the enzymatic activity of the reaction medium, after binding of the bindable substance to the binding protein, necessitates the use of one or more centrifugation steps which considerably increase the time taken for the determination; said processes may not be sufficiently sensitive when there is difficulty in separating insoluble particles from the reaction medium, notably owing to the nature and molecular weight of the binding substance.

Moreover, processes for the immobilization of enzymes on magnetic support are already known [Biotechnology and Bioengineering, Vol. XV (1973) and Biotechnology and Bioengineering Vol. XVI, p. 385–396 (1974)]. In these processes the enzyme is bound directly to the magnetic support; it is thus possible to use enzymes industrially, in fermentors for example; their conservation, recovery and reuse are then easy.

A magnetic gel suitable for immunoenzymatic or even radioimmunological determinations has now been discovered.

The gel according to the present invention is an acrylamide or agarose gel or a mixed acrylamide-agarose gel containing magnetic particles. Acrylamide and agarose gels and the mixed acrylamide-agarose gels are known and are notably useful as migration supports for electrophoretic separation of biological substances or for methods of immunochemical analysis in a gel medium (see French Pat. No. 1,483,742).

The gels of the invention are obtained by using known processes, the magnetic particles being incorporated in said gel while it is being formed, notably in the starting materials useful for obtaining same.

Thus, according to the preferred embodiment of the invention, a magnetic mixed acrylamide-agarose gel can be prepared using the process described by URIEL et al (C.R. Acad. Sc. Paris, v.273, pages 2358–2360, 1971 series D), the magnetic particles being added, according to the invention, to the acrylamide monomer. The magnetic gels of the present invention are advantageously spherical in shape with a mesh size in the range of from 50 to 500 μm.

The magnetic particles introduced into the gels according to the invention are, for example, magnetic, ferrite or iron powder particles; magnetite is particularly preferred. The amount of magnetic particles introduced into the gels of the invention is not critical; it should be sufficient to permit good separation of the gel from a liquid reaction medium by means of a magnet. As an example, it may be pointed out that an amount in the order of 20 g of magnetite for 10 grams of acrylamide monomer and 0.25 g of bisacrylamide is suited to the requirements of the invention when the gel is a polyacrylamide-agarose gel prepared according to the above-mentioned process.

The magnetic gel thus obtained can then be coupled with a protein by a coupling agent; the agents usually employed in this field are used as the coupling agent; amond said agents, glutaraldehyde may be mentioned.

The coupling of proteins and the magnetic gel according to the invention is advantageously effected using the method described by T. TERNYNCK and S. AVRAMEAS (F.E.B.S. letters, 23, 24, 1972).

The magnetic gel of the invention, coupled with a protein, for example an antibody or an antigen, is used for immunoenzymatic determinaton of the corresponding antibody or antigen. Another object of the invention is this magnetic-protein gel complex. For greater clarity in the present description, a magnetic gel coupled with an antigen will be referred to hereafter.

According to a preferred embodiment of the invention determination of the antibodies contained in a biological liquid is effected as follows:

A predetermined amount of magnetic gel coupled with the antigen is contacted with the biological liquid containing the said antibodies. After incubation for about 0.5 to 1 hour, the gel is washed several times with a phosphate buffer, the gel being maintained on the test tube walls by means of a magnetic field, this being possible owing to the presence of magnetic particles in the gel, and thus avoiding the centrifugation step necessary after each wash as in a conventional process of determination of this type. After said washes, the gel is incubated for about 30 minutes in the presence of antibodies labelled with an enzyme. Labelling of the antibodies with an enzyme is effected by a process well known to one man skilled in the art; the enzymes conventionally used in immunoenzymatic determination, such as glucose-oxidase and peroxidase, are used as enzymes. After incubation of the gel in the presence of antibodies labelled with an enzyme, the enzymatic activity of the gel is measured after removal of the supernatent by retaining the gel on the walls of the tube by means of a magnetic field; the enzymatic activity is determined by reading the optical density. Determinations take approximately 2 hours; the gel of the invention therefore enables the duration of conventional immunoenzymatic determinations to be reduced about four-fold.

The magnetic gels of the present invention can notably be used for determining anti-medicament, antiallergene and anti-parasitic IgE, specific anti-German measles IgMs making it possible to detect a recent attack of German measles during pregnancy; they also permit rapid determination of antibodies, tetanic anti-toxin, for example in persons who have been involved in acidents, or anti-ADN antibodies for example in the case of *Lupus erythematosus*.

It is also possible to seek the specificity of the antipollen allergy, for example of graminaceous plants (*Dactylis glomerata, Lolium perenne, Phleum pratense, Secale Cereale*) and to measure the intensity of an humoral reaction (strong or weak amount of specific IgE).

The magnetic gel of the invention can form part of a kit of reactants for immunoenzymatic determination;

this kit of reactants which constitutes another object of the invention is composed essentially:
- of magnetic gel coupled with an antigen or an antibody,
- a buffer,
- an antibody or an antigen specific to the antigen or antibody to be tested, coupled with an enzyme,
- a magnet,
- an enzyme substrate to reveal its enzymatic activity,
- normal control serum.

The kit can further contain accessories making it possible to carry out a series of dilutions of the sample to be determined. The invention will be illustrated in greater detail by the following non-limitative examples.

EXAMPLE 1

(a) Preparation of a ferromagnetic polyacrylamide-agarose gel.

The process described by URIEL et al (C.R. Acd. Sci. Paris, v.273, 2358–2360, 1971, series D) was used.

50 g of $Fe_3O_4$ was used for 10 g of acrylamide monomer, 0.25 g of bis-acrylamide and 5 g of agarose. The magnetite was added to the acrylamide and bis-acrylamide solution before the latter was mixed with the solution containing the melted agarose.

(b) Coupling of proteins with the magnetic gel so prepared

The gel thus obtained was coupled with proteins by means of glutaraldehyde according to the method devised by T. TERNYNCK and S. AVRAMEAS (F.E.B.S. Letters 23, 24, 1972). The following proteins were attached:
- sheep Ig
- sheep antibody, rabbit anti-Ig
- tetanic anatoxin
- bovine albumine.

The amounts of these bound substances are shown hereinafter as a function of the size of the magnetic gel particles.

| Diameter of the ferromagnetic polyacrylamide-agarose particles | Amount of bound sheep Ig | Amount of bound sheep antibody rabbit anti-Ig | Amount of bound tetanic anatoxin | Amount of bound bovine albumine |
|---|---|---|---|---|
| 500 : 250 μm | 1.5 mg/ml | | | |
| 250 : 125 μm | 3.1 mg/ml | | | |
| 125 : 63 μm | 3.1 mg/ml | 2.1 mg/ml | 0.75 mg/ml | 1.4 mg/ml |

EXAMPLE 2

Quantity determination of antibodies

The method of determination is as follows:

Each tube containing 50 μl of antigen bound to the magnetic gel receives 1 ml of a dilution of immune serum or normal serum (control).

After incubation for one hour at 20° C., the gel is washed three times with phosphate buffer (PBS). The gel is maintained on the walls of the tube by means of magnet during the washes.

The gel is then incubated for 30 minutes in the presence of anti-immunoglobulin antibodies labelled with glucose-oxidase.

The enzymatic reaction is effected on the gel after three further washes (PBS).

Reading of optical density is effected at 400 nm after 10 minutes enzymatic reaction at laboratory temperature. The enzymatic activity measured is compared with that of a control (normal serum).

The gel used was magnetic gel coupled with sheep Ig prepared according to example 1; said gel was incubated in accordance with the procedure described above with the rabbit immune serum sheep anti Ig and the optical density of the gel for different dilutions of this immune serum was noted. The results obtained are given in the single figure appended, which shows the optical density measured at 400 nm in ordinates and the dilutions in abscissa; curve (A) refers to the immune serum and curve (B) relates to the normal serum used as control.

Similar results were obtained using the gel coupled with the bovine albumine prepared according to Example 1 and immune serum of rabbit bovine albumin antiserum.

The sensitivity of the determination realized according to the invention is approximately 50 ng of antibodies per ml.

What we claim is:

1. A method for the immunoenzymatic assay of a biological liquid containing antibodies or antigens which comprises incubating said liquid in contact with a magnetic gel comprising particles of about 50 to 500 μm of a gel selected from the group consisting of polyacrylamide, agarose and mixtures thereof, magnetic particles embedded within the gel, protein molecules, and a coupling agent chemically linking the gel with embedded magnetic particles to the protein molecules, washing the gel so incubated, magnetically separating the gel from the washing medium, incubating the gel with enzyme-labelled antibodies or antigens, magnetically separating the gel, and measuring the enzyme activity of the gel, which indicates the content of antibodies or antigens contained in the liquid being assayed.

2. A method according to claim 1, where the biological liquid to be assayed contains an allergen or tetanic anatoxin.

3. A magnetic gel for immunoassays comprising particles of about 50 to 500 μm of a polyacrylamideagarose gel, magnetic particles embedded within the gel, said particles being selected from the group consisting of magnetite, ferrite and iron powder particles, protein molecules, and a coupling agent chemically linking the gel with embedded magnetic particles to the protein molecules.

4. A magnetic gel according to claim 3, wherein the coupling agent is glutaraldehyde.

5. A magnetic gel according to claim 3, wherein the magnetic particles are particles of magnetite and the protein is an antigen or an antibody which is coupled to the acrylamideagarose by means of glutaraldehyde.

* * * * *